Jan. 8, 1974 A. W. FISCHER Plant Pat. 3,429
AFRICAN VIOLET PLANT
Filed Jan. 24, 1972
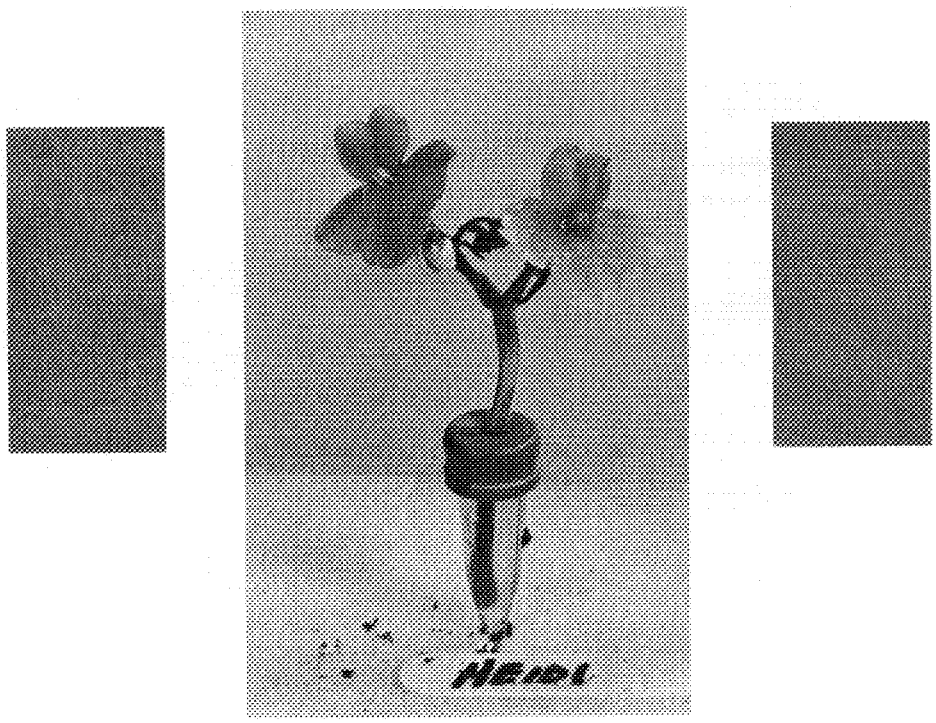
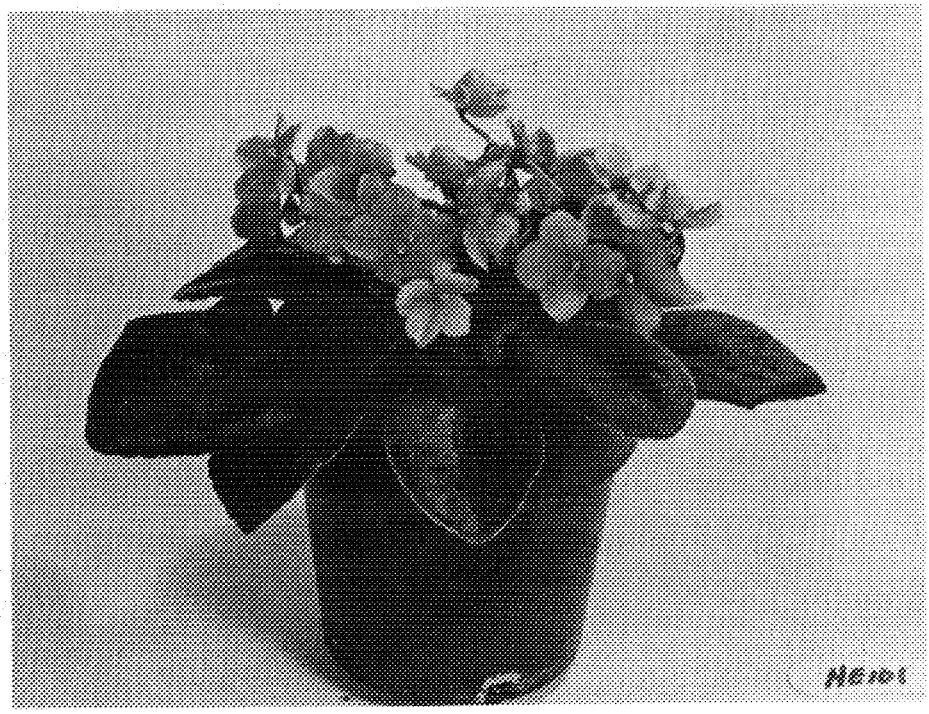

United States Patent Office

Plant Pat. 3,429
Patented Jan. 8, 1974

3,429

AFRICAN VIOLET PLANT

Arnold W. Fischer, Isernhagen, Germany, assignor to Geo. J. Ball, West Chicago, Ill.

Filed Jan. 24, 1972, Ser. No. 220,506
Int. Cl. A01h 5/00
U.S. Cl. Plt.—69 1 Claim

ABSTRACT OF THE DISCLOSURE

A new variety of African violet plant distinguished by its profuse, year around production of long lasting blossoms which appear on erect stalks displaying the flowers well above the plant foliage. The new plant flowers uniformly with large blossoms of a pleasing pink color.

BACKGROUND OF THE INVENTION

My new variety of African violet plant originated as a seedling developed by me at Isernhagen, Germany, in the course of my breeding and cultural efforts to produce improved varieties of African violet plants for the commercial potted plant market. This plant was observed to have a vigorous growth habit which produced a profuse display of relatively large flowers massed well above the foliage and having an attractive rich pink color. For these reasons, this plant was selected for testing and asexual propagation, under my direction, in greenhouse at Isernhagen, Germany, has demonstrated the new variety to have these and other advantages which hold true from generation to generation. Asexual propagation of this new plant by leaf cuttings has been done successfully by my licensee at West Chicago, Ill., U.S.A., and commercial production of the plant, by leaf cuttings and division of shoots, is now being done by my said licensee at West Chicago, Ill., with no noticeable deviation from the distinctive characteristics of the original plant produced by me.

DESCRIPTION OF THE DRAWING

My new variety of African violet plant is illustrated by the accompanying drawing which shows the color and form characteristics of the blossoms and plant, the color rendition being as nearly true as is reasonably possible to obtain by conventional photographic procedures. The uppermost view shows the manner in which the flowers are carried by the relatively strong stalk; and the lower view shows the dense and spreading form of the plant with its display of closely gathered blossoms. Color patches A and B show the true colors of the top side and reverse side, respectively, of the flower petals.

DESCRIPTION OF THE NEW PLANT

The following is a detailed description of my new variety of African violet plant with color designations according to the Horticultural Color Chart published by the British Colour Council in collaboration with the Royal Horticultural Society.

*The plant*

Origin: Seedling
Parentage:
- *Seed parent.*—An unnamed double pink (unpatented)
- *Pollent parent.*—An unnamed single pink (unpatented)

Classification:
- *Botanic.*—*Saintpaulia ionantha*
- *Commercial.*—African violet Form: Compact and spreading potted plant
Height: 3 inches from base to top of flowers
Growth: Vigorous and condensed with sturdy upright flower stalks
Foliage:

- *Quantity.*—Abundant
- *Size of leaf.*—Varies greatly with age of leaf
- *Shape of leaf.*—Oblong-ovate, some almost heart-shaped, with crenate margins
- *Texture.*—Tomentose
- *Veins.*—Pinnate
- *Color.*—Upper side—Ivy Green 0001060/2. Under side—Maroon 1030/3
- *Petioles.*—1½ to 2 inches long

*The bud*

Form: Bell-shaped
Size: Fairly small—3/16 to ¼ inch in diameter and ¼ inch deep
Opening rate: Very slow—5 weeks from visible bud to opening of flower
Color: When petals begin to unfurl—Rhodamine Pink 527/2
Sepals: Hooded over bud for a very short time
- *Form.*—Upstanding, branched and spear-shaped
- *Color.*—Inside—Parsley Green 00962/1. Outside—Maroon 1030

Calyx:
- *Shape.*—Funnel-shaped and splits to star shape
- *Aspect.*—Smooth on inside, hairy on outside Peduncle: Sturdy, erect and very tomentose
- *Length.*—½ to ¾ inch from stalk to flower
- *Color.*—Maroon 1030

*The flower*

Blooming character: Recurrent and profuse the year around, with production of 30 to 40 flowers on a well grown plant 25 to 30 weeks old
Size of flower: Size varies on the plant with most blooms fairly large
- *Diameter.*—1 1/16 to 1½ inches
- *Depth.*—To ¼ inch—mostly flat Borne: In cluster on each peduncle
Shape: Cup-shaped, almost flat, when first opening and becomes flat when fully opened
Petalage: Number—5, three noticeably larger than remaining two
- *Arrangement.*—Sympetalous
- *Form.*—Rotate and bilaterally symmetrical with smooth margins
- *Color.*—Top side—Cyclamen Purple 30/2 becoming more intense near center of flower. Reverse side—Rhodamine Purple 29/2

Texture: Soft and smooth
Appearance: Velvety and glistens, tomentose or under side
Peduncle: Generally upright, ½ to ¾ inch long for each flower and extending from stalk branch 1⅜ to 2 inches long
- *Strength.*—Sturdy—but flexible
- *Color.*—Maroon 1030

Discoloration after full bloom: Color tends to fade
Effect of weather: Hot weather fades the flower and suppresses flowering. Plant thrives in 80 to 90% humidity.
Fragrance: None
Lasting quality: Open flower—10 to 14 days
Persistence: Flower hangs on and dries on the stalk

*Reproductive organs*

Stamens:
- *Anthers.*—Basified, 2 in number, each 1/16 inch long and composed of two anther cells
- *Filaments.*—3/16 inch long, Sap Green 62/2 in color
- *Pollen.*—Color—White Pistils: One—⅜ inch long
Stigmas: Color: Rhodamine Purple 29/2
Style: Length: 3/16 inch. Color: Rhodamine Purple 29/2
Ovaries: Superior and tomentose The principal features of my new variety of African violet plant are its profuse and uniform flowering habit, its vigorous growth, and its display of closely grouped flowers extending well above the foliage mass. The flowers are of an attractive pink color and the petal veins provide a mild striping effect which pleasantly characterizes the blooms. This new variety is further distinguished by its earlier flowering habit, which enhances its commercial value, and the relatively longer lasting quality of the blooms.

I claim:

1. A new and distinct variety of African violet plant, substantially as herein shown and described, characterized by its profuse and uniform year around production of relatively large flowers which appear well above a flat growth of leaves, its early flowering habit, and the long lasting quality of the blooms.

No references cited.

ROBERT E. BAGWILL, Primary Examiner